United States Patent
Wright et al.

(10) Patent No.: US 7,988,673 B2
(45) Date of Patent: Aug. 2, 2011

(54) PROTECTIVE DRESSING AND METHODS OF USE THEREOF

(75) Inventors: Clifford A. Wright, San Diego, CA (US); Gene Stewart, San Marcos, CA (US)

(73) Assignee: Venetec International, Inc., Covington, GA (US)

( * ) Notice: Subject to any disclaimer, the term of this patent is extended or adjusted under 35 U.S.C. 154(b) by 1693 days.

(21) Appl. No.: 11/183,165

(22) Filed: Jul. 14, 2005

(65) Prior Publication Data

US 2007/0055205 A1    Mar. 8, 2007

(51) Int. Cl.
*A61M 5/32*    (2006.01)
(52) U.S. Cl. .................. 604/174; 602/48; 424/449
(58) Field of Classification Search .............. 424/447, 424/449; 602/48; 604/174
See application file for complete search history.

(56) References Cited

U.S. PATENT DOCUMENTS

| | | |
|---|---|---|
| 695,270 A | 3/1902 | Beringer |
| 1,706,634 A | 3/1928 | Seils |
| 2,367,690 A | 1/1945 | Purdy |
| 2,402,306 A | 6/1946 | Turkel |
| 3,046,984 A | 7/1962 | Eby |
| 3,194,235 A | 7/1965 | Cooke |
| 3,461,869 A | 8/1969 | Hargest |
| 3,537,452 A | 11/1970 | Wilks |
| 3,568,679 A | 3/1971 | Reif |
| 3,630,195 A | 12/1971 | Santomieri |
| 3,645,835 A | 2/1972 | Hodgson |
| 3,782,383 A | 1/1974 | Thompson et al. |
| 3,826,254 A | 7/1974 | Mellor |
| 3,900,026 A | 8/1975 | Wagner |
| 3,901,226 A | 8/1975 | Scardenzan |
| 3,910,538 A | 10/1975 | Baitella |
| 4,059,105 A | 11/1977 | Cutruzzula et al. |
| 4,082,094 A | 4/1978 | Dailey |
| 4,084,911 A | 4/1978 | DeWitt |
| 4,129,128 A | 12/1978 | McFarlane |
| D252,822 S | 9/1979 | McFarlane |
| 4,193,174 A | 3/1980 | Stephens |
| 4,224,937 A | 9/1980 | Gordon |
| 4,250,880 A | 2/1981 | Gordon |
| 4,277,102 A | 7/1981 | Aras |

(Continued)

FOREIGN PATENT DOCUMENTS

CA    1 311 977    12/1992

(Continued)

OTHER PUBLICATIONS

U.S. Patent and Trademark Office; Combined International Search Report and Written Opinion for PCT/US2006/026995; Feb. 2, 2007.

(Continued)

*Primary Examiner* — Nicholas D Lucchesi
*Assistant Examiner* — Gerald Landry, II
(74) *Attorney, Agent, or Firm* — Knobbe, Martens, Olson & Bear LLP (57) ABSTRACT

A protective device having a substantially rigid casing for placement on a patient's skin, wherein the casing has a hollow interior facing the patient's skin and a lip. The casing can be spanned across its hollow interior by a membrane. The casing can have a first adhesive seal attached to a bottom surface of the lip of the casing, and a second adhesive seal attached to the top surface of the lip of the casing.

19 Claims, 6 Drawing Sheets

U.S. PATENT DOCUMENTS

| | | | |
|---|---|---|---|
| 4,316,461 A | 2/1982 | Marais et al. | |
| 4,333,468 A | 6/1982 | Geist | |
| 4,392,853 A | 7/1983 | Muto | |
| 4,449,975 A | 5/1984 | Perry | |
| 4,470,410 A | 9/1984 | Elliott | |
| 4,484,913 A | 11/1984 | Swauger | |
| 4,516,968 A | 5/1985 | Marshall et al. | |
| 4,517,971 A | 5/1985 | Sorbonne | |
| 4,563,177 A | 1/1986 | Kamen | |
| 4,585,443 A | 4/1986 | Kaufman | |
| 4,614,183 A | 9/1986 | McCracken et al. | |
| 4,632,670 A | 12/1986 | Muller | |
| 4,633,863 A | 1/1987 | Filips et al. | |
| 4,645,492 A | 2/1987 | Weeks | |
| 4,666,434 A | 5/1987 | Kaufman | |
| 4,667,666 A * | 5/1987 | Fryslie | 128/888 |
| 4,669,458 A | 6/1987 | Abraham | |
| 4,679,553 A | 7/1987 | Proulx | |
| 4,711,636 A | 12/1987 | Bierman | |
| 4,737,143 A | 4/1988 | Russell | |
| 4,781,695 A | 11/1988 | Dalton | |
| 4,846,807 A | 7/1989 | Safadago | |
| 4,852,844 A | 8/1989 | Villaveces | |
| 4,863,432 A | 9/1989 | Kvalo | |
| 4,870,976 A | 10/1989 | Denny | |
| 4,878,897 A | 11/1989 | Katzin | |
| 4,898,587 A | 2/1990 | Mera | |
| 4,913,393 A | 4/1990 | Wood | |
| 4,976,698 A | 12/1990 | Stokley | |
| 4,976,700 A | 12/1990 | Tollini | |
| 4,997,421 A | 3/1991 | Palsrok et al. | |
| 5,029,941 A | 7/1991 | Twisselmann | |
| 5,037,397 A | 8/1991 | Kalt et al. | |
| 5,074,847 A | 12/1991 | Greenwell et al. | |
| 5,084,026 A | 1/1992 | Shapiro | |
| 5,112,313 A | 5/1992 | Sallee | |
| 5,116,324 A | 5/1992 | Brierley et al. | |
| 5,137,519 A | 8/1992 | Littrell et al. | |
| 5,167,240 A | 12/1992 | Rozier et al. | |
| 5,192,273 A | 3/1993 | Bierman | |
| 5,192,274 A | 3/1993 | Bierman | |
| 5,215,532 A | 6/1993 | Atkinson | |
| 5,230,350 A * | 7/1993 | Fentress | 128/846 |
| 5,238,010 A | 8/1993 | Grabenkort et al. | |
| 5,281,001 A | 1/1994 | Bergsten et al. | |
| 5,290,248 A | 3/1994 | Bierman et al. | |
| D347,060 S | 5/1994 | Bierman | |
| 5,314,411 A | 5/1994 | Bierman et al. | |
| 5,328,487 A | 7/1994 | Starchevich | |
| 5,339,834 A | 8/1994 | Marcelli | |
| 5,354,282 A | 10/1994 | Bierman | |
| 5,356,391 A | 10/1994 | Stewart | |
| 5,370,627 A | 12/1994 | Conway | |
| 5,395,344 A | 3/1995 | Beisang et al. | |
| 5,407,249 A | 4/1995 | Bonutti | |
| 5,413,120 A | 5/1995 | Grant | |
| 5,413,562 A | 5/1995 | Swauger | |
| D359,120 S | 6/1995 | Sallee et al. | |
| 5,449,349 A | 9/1995 | Sallee et al. | |
| D363,543 S | 10/1995 | Van Funderburk et al. | |
| 5,456,671 A | 10/1995 | Bierman | |
| 5,462,247 A | 10/1995 | Aldrich | |
| D364,922 S | 12/1995 | Bierman | |
| 5,480,719 A | 1/1996 | Tollini | |
| D375,355 S | 11/1996 | Bierman | |
| D375,356 S | 11/1996 | Bierman | |
| 5,577,516 A | 11/1996 | Schaeffer | |
| 5,578,013 A | 11/1996 | Bierman | |
| D377,125 S | 1/1997 | Adamsson | |
| D377,831 S | 2/1997 | Bierman | |
| 5,605,546 A | 2/1997 | Wolzinger et al. | |
| 5,664,581 A | 9/1997 | Ashley | |
| 5,681,290 A | 10/1997 | Alexander | |
| 5,685,859 A | 11/1997 | Kornerup | |
| 5,686,096 A | 11/1997 | Khan et al. | |
| 5,690,616 A | 11/1997 | Mogg | |
| 5,693,032 A | 12/1997 | Bierman | |
| 5,702,371 A | 12/1997 | Bierman | |
| 5,713,591 A | 2/1998 | Zarkhin et al. | |
| 5,722,959 A | 3/1998 | Bierman | |
| 5,728,053 A | 3/1998 | Calvert | |
| 5,733,571 A * | 3/1998 | Sackler | 424/449 |
| 5,776,106 A | 7/1998 | Matyas | |
| 5,800,402 A | 9/1998 | Bierman | |
| 5,800,410 A | 9/1998 | Gawreluk | |
| 5,810,781 A | 9/1998 | Bierman | |
| D399,954 S | 10/1998 | Bierman | |
| 5,827,230 A | 10/1998 | Bierman | |
| 5,827,239 A | 10/1998 | Dillon et al. | |
| 5,833,666 A | 11/1998 | Davis et al. | |
| 5,833,667 A | 11/1998 | Bierman | |
| 5,855,591 A | 1/1999 | Bierman | |
| 5,885,254 A | 3/1999 | Matyas | |
| 5,897,519 A | 4/1999 | Shesol et al. | |
| 6,050,934 A | 4/2000 | Mikhail et al. | |
| D425,619 S | 5/2000 | Bierman | |
| 6,096,943 A * | 8/2000 | Maiwald | 602/48 |
| 6,099,509 A | 8/2000 | Brown et al. | |
| 6,113,577 A | 9/2000 | Hakky et al. | |
| 6,123,690 A | 9/2000 | Mejslov | |
| 6,132,398 A | 10/2000 | Bierman | |
| 6,132,399 A | 10/2000 | Shultz | |
| 6,213,979 B1 | 4/2001 | Bierman | |
| 6,224,571 B1 | 5/2001 | Bierman | |
| 6,231,547 B1 | 5/2001 | O'Hara | |
| 6,231,548 B1 | 5/2001 | Bassett | |
| 6,241,697 B1 * | 6/2001 | Augustine | 602/2 |
| 6,255,552 B1 * | 7/2001 | Cummings et al. | 602/58 |
| 6,258,066 B1 | 7/2001 | Urich | |
| 6,264,977 B1 * | 7/2001 | Hoffmann | 424/447 |
| 6,283,945 B1 | 9/2001 | Bierman | |
| 6,290,676 B1 | 9/2001 | Bierman | |
| 6,322,539 B1 | 11/2001 | Cook | |
| 6,361,523 B1 | 3/2002 | Bierman | |
| 6,375,639 B1 | 4/2002 | Duplessie | |
| 6,413,240 B1 | 7/2002 | Bierman et al. | |
| 6,428,515 B1 | 8/2002 | Bierman et al. | |
| 6,428,516 B1 | 8/2002 | Bierman et al. | |
| 6,436,073 B1 | 8/2002 | Teichert | |
| 6,447,485 B2 | 9/2002 | Bierman | |
| 6,447,486 B1 | 9/2002 | Tollini | |
| 6,458,104 B2 | 10/2002 | Gautsche | |
| 6,471,676 B1 | 10/2002 | DeLegge et al. | |
| 6,482,183 B1 | 11/2002 | Pausch | |
| 6,491,664 B2 | 12/2002 | Bierman | |
| 6,500,154 B1 | 12/2002 | Hakky et al. | |
| D469,530 S | 1/2003 | Gomez | |
| D470,936 S | 2/2003 | Bierman | |
| 6,517,522 B1 | 2/2003 | Bell et al. | |
| 6,551,285 B1 | 4/2003 | Bierman | |
| 6,572,588 B1 | 6/2003 | Bierman et al. | |
| 6,582,403 B1 | 6/2003 | Bierman et al. | |
| 6,616,635 B1 | 9/2003 | Bell et al. | |
| 6,619,598 B2 | 9/2003 | De Miranda | |
| 6,619,747 B2 | 9/2003 | Ko et al. | |
| 6,626,890 B2 | 9/2003 | Nguyen et al. | |
| 6,652,487 B1 | 11/2003 | Cook | |
| 6,663,600 B2 | 12/2003 | Bierman et al. | |
| 6,689,104 B2 | 2/2004 | Bierman | |
| 6,700,032 B1 | 3/2004 | Gray | |
| D492,411 S | 6/2004 | Bierman | |
| 6,770,055 B2 | 8/2004 | Bierman et al. | |
| 6,786,892 B2 | 9/2004 | Bierman | |
| 6,809,230 B2 | 10/2004 | Hancock et al. | |
| 6,827,705 B2 | 12/2004 | Bierman | |
| 6,827,706 B2 | 12/2004 | Tollini | |
| 6,827,707 B2 | 12/2004 | Wright et al. | |
| 6,834,652 B2 | 12/2004 | Altman | |
| 6,837,875 B1 | 1/2005 | Bierman | |
| 6,855,135 B2 * | 2/2005 | Lockwood et al. | 604/313 |
| 6,866,652 B2 | 3/2005 | Bierman | |
| D503,977 S | 4/2005 | Bierman | |
| 6,951,550 B2 | 10/2005 | Bierman | |
| 6,972,003 B2 | 12/2005 | Bierman | |
| 6,979,320 B2 | 12/2005 | Bierman | |
| 6,981,969 B2 | 1/2006 | Chavez et al. | |
| 7,014,627 B2 | 3/2006 | Bierman | |

| | | |
|---|---|---|
| 7,018,362 B2 | 3/2006 | Bierman |
| 7,070,580 B2 | 7/2006 | Nielsen |
| 7,090,660 B2 | 8/2006 | Roberts et al. |
| D528,206 S | 9/2006 | Bierman |
| 7,153,291 B2 | 12/2006 | Bierman |
| 7,354,421 B2 | 4/2008 | Bierman |
| 2001/0011164 A1 | 8/2001 | Bierman |
| 2002/0068904 A1 | 6/2002 | Bierman et al. |
| 2002/0099360 A1 | 7/2002 | Bierman |
| 2003/0055382 A1 | 3/2003 | Schaeffer |
| 2003/0069529 A1* | 4/2003 | Augustine et al. .............. 602/48 |
| 2003/0229313 A1 | 12/2003 | Bierman |
| 2004/0102736 A1 | 5/2004 | Bierman |
| 2004/0111067 A1 | 6/2004 | Kirchhofer |
| 2004/0138624 A1 | 7/2004 | Bierman |
| 2004/0143220 A1* | 7/2004 | Worthley ..................... 604/174 |
| 2004/0158209 A1 | 8/2004 | Wright |
| 2004/0167475 A1 | 8/2004 | Wright et al. |
| 2004/0204685 A1 | 10/2004 | Wright et al. |
| 2005/0182367 A1 | 8/2005 | Walborn |
| 2005/0215953 A1 | 9/2005 | Rossen |
| 2005/0288635 A1 | 12/2005 | Davis et al. |
| 2006/0015076 A1 | 1/2006 | Heinzerling et al. |
| 2006/0064063 A1 | 3/2006 | Bierman |
| 2006/0084922 A1 | 4/2006 | Botha |
| 2006/0135944 A1 | 6/2006 | Bierman |
| 2006/0184127 A1 | 8/2006 | Bierman |
| 2006/0184129 A1 | 8/2006 | Bierman |
| 2006/0217669 A1 | 9/2006 | Botha |
| 2006/0247577 A1 | 11/2006 | Wright |
| 2006/0264836 A1 | 11/2006 | Bierman |
| 2006/0270995 A1 | 11/2006 | Bierman |
| 2009/0048563 A1* | 2/2009 | Ethelfeld et al. .............. 604/174 |

FOREIGN PATENT DOCUMENTS

| | | |
|---|---|---|
| CA | 1 318 824 | 6/1993 |
| EP | 0356683 | 3/2000 |
| WO | WO 94/21319 | 9/1994 |
| WO | WO 97/15337 | 5/1997 |
| WO | WO 99/55409 | 11/1999 |

OTHER PUBLICATIONS

Venetec Statlock Instructional Sheets; statlock.com/products.html; "IV Select; IV Ultra; IV Plus; IV; Intima; IV-K; Arterial Plus; CV Plus; CV Ultra; PICC Plus Patient User Guide."

Paul et al. "Chitosan and Alginate Wound Dressings: a short review" *Trends Biomater. Artif.* Organs. 18:18-23 (2004).

* cited by examiner

PROTECTIVE DRESSING AND METHODS OF USE THEREOF

TECHNICAL FIELD

This application generally relates to devices for protecting inserted medical devices, wounds, burns, ulcers and the like. More particularly, this application relates to an improved device having one or more adhesive layers and a substantially rigid casing for affixing and covering inserted and applied medical devices, external attachments of inserted and applied medical devices, wounds, burns, ulcers and the like.

BACKGROUND

Inserted and applied medical devices are indispensable in modern-day medical practice. Inserted medical devices can include implantable ports, intravascular catheters, percutaneous tubing such as nephrostomy tubes, gastrostomy tubes, or colostomy tubes and the like, indwelling catheters, epidural catheters and external fixator pins. Inserted medical devices can put patients at risk for serious complications due to local and systemic infections, thrombosis and thrombophlebitis. They also can cause pain and discomfort due to inward pressure or compression or snagging of an exit site catheter tail. Applied medical devices such as electrodes that can be used to monitor heart conditions, brain activity or fetal movement, likewise can cause discomfort and are at risk for compression, snagging and inadvertent removal.

Inserted medical devices such as intravascular catheters can be used to administer long-term or repeated treatments such as chemotherapy, blood transfusions or blood draws, administration of high-calorie liquids and antibiotics while avoiding the need to start an IV each time. Although such devices provide convenient access, their use often negatively impacts patient well-being. Exemplary intravascular catheters include central vascular catheters, peripheral vascular catheters, midline catheters, peripherally inserted central catheters, hemodialysis catheters, pulmonary catheters, umbilical catheters and scalp vein catheters.

Another inserted medical device is an implantable port. An implantable port sits under the skin and connects to a catheter cannulating a large blood vessel. The port can be felt as a small bump underneath the skin and specialized needles, such as a Huber needle, can be used to access the port to administer treatments directly into the bloodstream. For short term treatments, the needle is withdrawn from the port. For longer treatments, the needle can be left in place connected to the port.

Regardless of the type of applied or inserted medical device in use, each requires some means of securement to the patient. Film dressing is well known for the purpose of covering medical devices and external attachments. Transparent, semi-permeable polyurethane dressings have become a popular means of dressing insertion sites (see, for example, U.S. Pat. Nos. 4,614,183 and 3,645,835). Transparent dressings help to secure devices, allow for continuous visual inspection of the device, permit patients to bathe and shower without saturating the dressing, and provide some limited protection against infection. However, there is a need for dressings that can prevent compression, constriction and pain associated with the inadvertent manipulation of the medical devices while also providing adequate protection from infection, snagging and dislodgement.

Improvements in dressings for wounds due to burns, chronic ulcers, donor sites, post-operative wounds, and a variety of other injuries are likewise needed. Trends in modern medical practice have shown that healing of wounds may be significantly improved by clinical intervention using methods and materials that optimize wound conditions to support the physiological processes of the progressive stages of wound healing. Wound dressings are generally classified as passive, interactive or bioactive products. Traditional wound dressings like gauze and tulle dressings are examples of passive products. These dressings are helpful in collecting heavy exudate drainage, but they require frequent changing, cause irritation and have a tendency to stick to the wound during body movement and dressing removal. Interactive dressing products can include polymeric films, hydrocolloid dressings and hydrogels. These types of materials are mostly transparent, permeable to water vapor and oxygen and impermeable to bacteria. These films are recommended for low exuding wounds in that they are typically overwhelmed by the accumulated exudate moisture during the heavy drainage phase of wound healing. Bioactive dressings deliver substances active in wound healing. Bioactive dressings can deliver therapeutic compounds or the dressing itself can be constructed from material having endogenous wound healing properties.

There is a need for improved dressings for the purposes of protecting inserted and applied medical devices, affixing external attachments as well as protecting wounds on patients with extensive burns, lacerations and skin damage.

SUMMARY

Among the embodiments disclosed herein is a protective device having a substantially rigid casing for placement on a patient's skin. The casing can be made of a transparent, semi-transparent or translucent material and can be a variety of shapes including, but not limited to, spherical, cuboidal, triangular, pyramidal, cylindrical, conical and dome shaped. The casing has a hollow interior facing the patient's skin and a lip. A membrane spans the hollow interior of the casing and can be made of a transparent, semi-transparent or translucent material. An adhesive seal can be attached to a bottom surface of the lip of the casing and another adhesive seal attached to the top surface of the lip of the casing. Each of the casing, membrane, first adhesive seal and second adhesive seal of the disclosed protective device can include a notch. The notches can be aligned with one another forming a slot. The membrane and adhesive seals can be impregnated or coated with an antimicrobial, such as β-lactams antibiotics, penicillins, cephalosporins, carbapenems, monobactams, glycopeptides, aminoglycosides, macrolides, tetracyclines, chloramphenicols, clindamycins, vancomycins, streptogramins, oxazolindinones, fluoroquinolones, metronidazoles, sulfonamides, allylamines, non-azole ergosterol biosynthesis inhibitors, antimetabolite antifungals, flucytosine, azole antifungals, fluconazole, glucan synthesis inhibitors, caspofungin, polyene antifungals, amphotericin B, griseofulvin, antiseptic solutions, chloroxylenol, benzalkonium chloride, chlorhexidine, hexachlorophine, sulfadiazine, iodine compounds, mercury compounds, alcohol, hydrogen peroxide, boric acid, volatile oils, methyl salicylate, heavy metals and silver.

Also disclosed herein is a method of protecting a medical device. The method can include protecting medical devices including, but not limited to, an intravascular catheter, implantable port, needle, tubing, central vascular catheter, peripheral vascular catheter, midline catheter, peripherally inserted central catheter, hemodialysis catheter, pulmonary catheter, umbilical catheter, scalp vein catheter, percutaneous tubing, nephrostomy tube, gastrostomy tube, colostomy tube, tracheostomy tube, indwelling catheter, epidural catheter, external fixator pin and electrode. The method can include the step of positioning over a medical device on a patient's skin a substantially rigid casing, wherein the casing has a hollow interior facing the patient's skin, a lip, an adhesive seal attached to a bottom surface of the lip and a membrane spanning the hollow interior of the casing. The method can also include the step of securing a medical device with the membrane spanning the hollow interior of the casing. The method includes the step of adhering the casing to the patient's skin. The casing can be adhered to the patient's skin with an adhesive seal. A second adhesive seal can be attached to a top surface of the lip of the casing to further secure the casing to the patient's skin. Each of the casing and the membrane can be made of a transparent, semi-transparent or translucent material. Further, the casing can be a variety of shapes including, but not limited to, spherical, cuboidal, triangular, pyramidal, cylindrical, conical and dome shaped. Each of the casing, membrane, first adhesive seal and second adhesive seal can include a notch and the notches can be aligned with one another forming a slot.

A method is also provided for protecting a wound. The method includes the step of positioning on a patient's skin a substantially rigid casing, wherein the casing has a hollow interior facing the patient's skin, a lip, an adhesive seal attached to a bottom surface of the lip and a membrane spanning the hollow interior. The method includes the step of adhering the casing to the patient's skin. The casing can be adhered to the patient's skin with an adhesive seal. A second adhesive seal can be attached to a top surface of the lip of the casing to further secure the casing to the patient's skin. Each of the casing and the membrane can be made of a transparent, semi-transparent or translucent material. Further, the casing can be a variety of shapes including, but not limited to, spherical, cuboidal, triangular, pyramidal, cylindrical, conical and dome shaped.

Also disclosed herein is a kit that includes a protective device and instructions for applying the protective device to an individual's skin. The protective device can include a substantially rigid casing, wherein the casing has a hollow interior, a lip, a first adhesive seal attached to a bottom surface of the lip and a membrane spanning the hollow interior. The protective device also can include a second adhesive seal for further securing the casing to an individual's skin. The protective device also can include a backing on which the casing and second adhesive seal are removeably attached. Each of the membrane and the casing can be made of a transparent, semi-transparent or translucent material. The casing can be a variety of shapes including, but not limited to, spherical, cuboidal, triangular, pyramidal, cylindrical, conical and dome shaped. Each of the casing, membrane, first adhesive seal and second adhesive seal of the disclosed protective device can include a notch. The notches can be aligned with one another forming a slot. The membrane can be coated or impregnated with an antimicrobial agent.

DETAILED DESCRIPTION

Unless defined otherwise, all technical and scientific terms used herein have the same meaning as is commonly understood by one of skill in the art to which the disclosed device(s) belong. Disclosed are various devices and methods for affixing, covering and protecting inserted and applied medical devices, external attachments of inserted and applied medical devices, wounds, burns, ulcers and the like.

Figure 1:
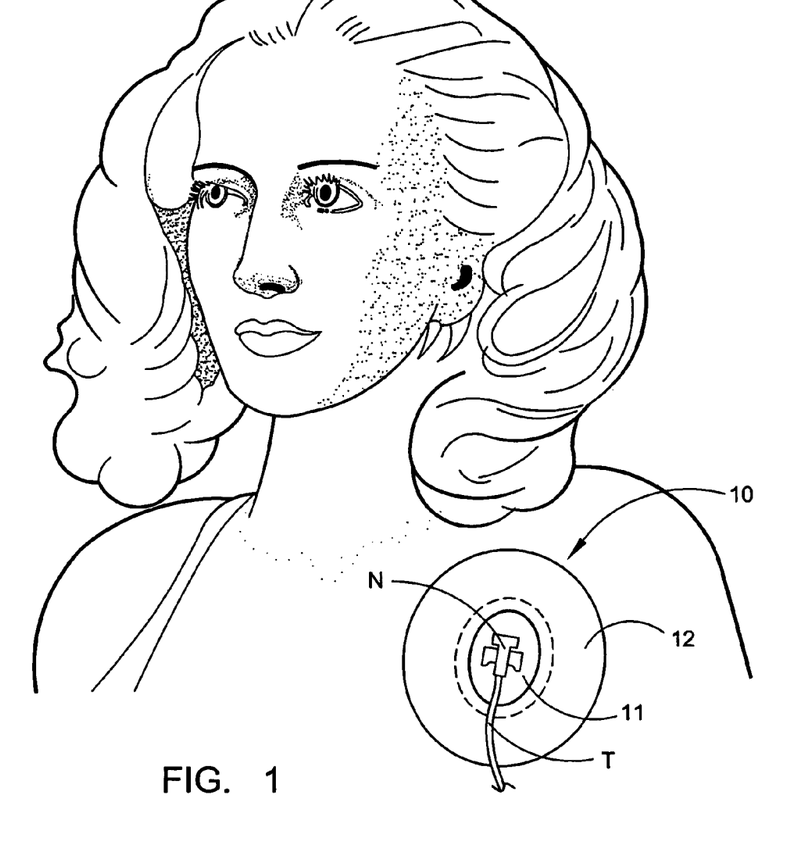
FIG. 1 is an illustration of one embodiment of a protective dressing covering a needle with attached tubing inserted into an implantable port in the chest of a patient.
Figure 2:
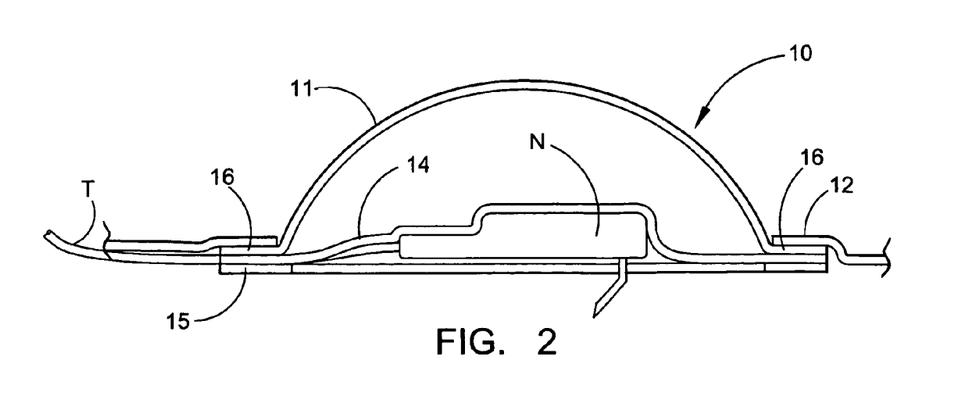
FIG. 2 is a side elevation view of the protective dressing of FIG. 1.

FIG. 1 shows a protective dressing 10 adhered to the chest of a patient covering an inserted medical device with external attachments (needle N and tubing T). The protective dressing 10 prevents accidental dislodgement and/or removal of an inserted medical device due to external attachments being snagged by clothing, for example, a bra strap worn by a female patient. Although the Figures show an exemplary device as having a dome shape, the device can be shaped differently than what is shown in the figures. For example, the device can also have a spherical, cuboidal, triangular, pyramidal, cylindrical and conical shape.

Figure 3:
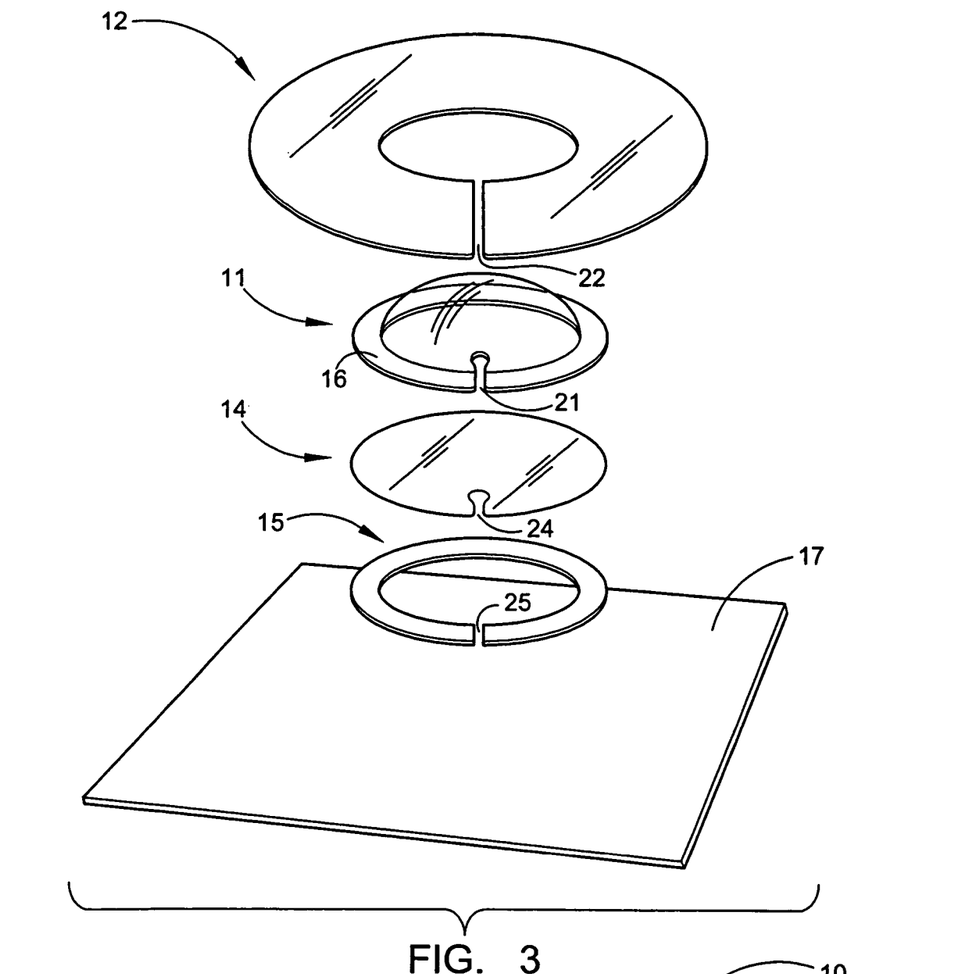
FIG. 3 is an exploded view of one embodiment of a protective dressing.
Figure 4:
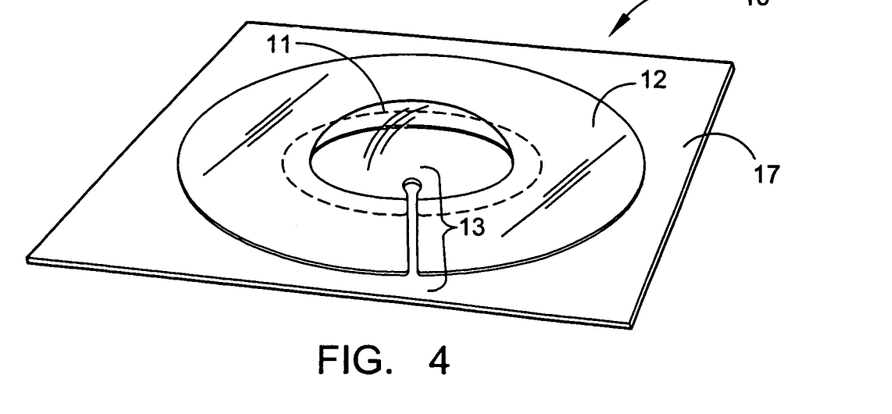
FIG. 4 is a perspective view of the protective dressing of FIG. 3.
Figure 5:
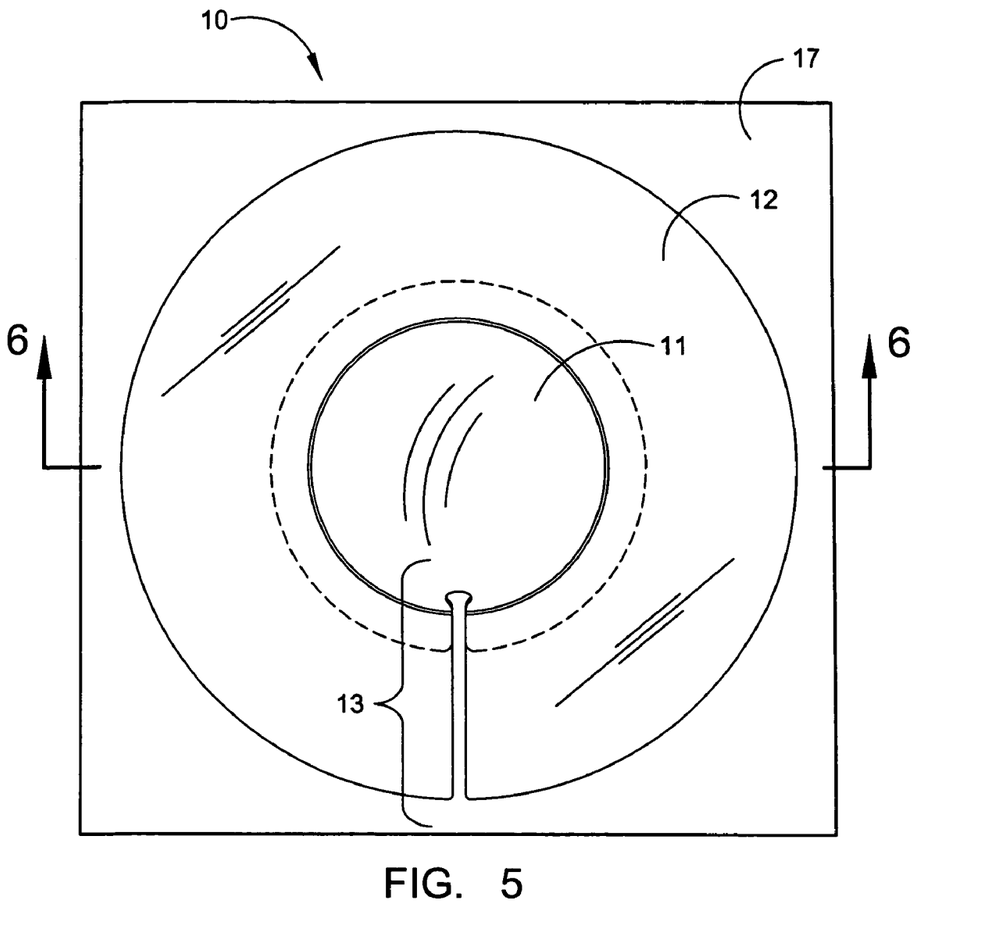
FIG. 5 is a top plane view of the protective dressing of FIG. 3.
Figure 6:
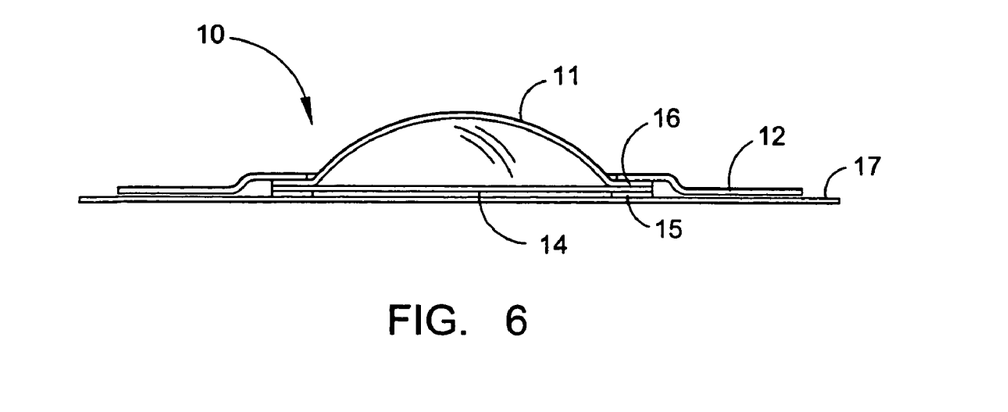
FIG. 6 is a cross-sectional view of the protective dressing of FIG. 5 taken along the line 6-6.

As shown in FIGS. 2, 3, 4, 5 and 6, the protective dressing 10 can include a substantially rigid casing 11 having a lip 16, a membrane 14, an internal seal 15 and external seal 12. As best illustrated in FIGS. 3 and 4, the casing 11 has a hollow interior spanned by a membrane 14. The membrane 14 attaches to the casing 11 at the lip 16 by, for example, an adhesive material coating the membrane 14 or due to adhesive properties of the membrane 14 itself. The internal seal 15 is shaped similarly as the lip 16 of the casing 11 and is attached to the bottom of the lip 16 of the casing 11 via the outer margin of the membrane 14, which is attached to the lip 16. Thus, the internal seal 15 and the lip 16 of the casing 11 sandwich the membrane 14. As described for the membrane 14, the internal seal 15 can be attached to the casing 11 by way of an adhesive material coating the internal seal 15, intrinsic-adhesive properties of the internal seal 15 itself or due to an adhesive coating or adhesive properties of the membrane 14.

The external seal 12 surrounds the outer protuberance of the casing 11. The external seal 12 contacts the top of the lip 16 of the casing 11 (i.e., the side of the lip 16 opposite of the internal seal 15 and the membrane 14). The external seal 12 can be attached to the lip 16 due to an adhesive coating on the bottom side of the external seal 12 or other adhesive property of the external seal 12. The external seal 12, internal seal 15 and membrane 14 can be made of adhesive material or coated with an adhesive material. The adhesive parts of the protective dressing 10 can be removeably attached to a backing 17, such as a wax paper backing and the like.

The hollow interior of the casing 11, as it relates to a patient, faces the patient's skin. The outer protuberance of the casing 11 faces away from the patient's skin. The casing 11 adheres to the patient's skin via the internal seal 15, the membrane 14 and the external seal 12. The membrane 14 adheres to both the patient's skin and an applied or inserted medical device and external attachments, for example, a needle N and tubing T. The lip 16 of the casing 11 surrounds the site of the applied or inserted medical device.

The protective dressing 10 can come in a variety of sizes to accommodate different applied or inserted medical devices and external attachments. For example, the protective dressing 10 and, in turn, the casing 11 can be proportionally sized to cover medical devices and attachments used in the art without excessive inward compression of the medical devices or attachments.

The casing 11 and the protective dressing 10 can come in a variety of shapes to accommodate the medical devices being protected including: spherical, cuboidal, triangular, pyramidal, cylindrical and conical shapes. In one embodiment, the casing 11 can be dome shaped (as shown in the Figures). The casing 11 can be made of a translucent, semi-transparent or transparent material. This allows for a medical practitioner or the patient to visually inspect the site of the protected device for signs of trouble such as clotting, breakage, signs of infection of the surrounding skin, accidental dislodgement, bleeding or discharge from the wound site. The casing 11 can be made of various rigid materials exhibiting high tensile, high compressive and high shear strength as well as high impact properties. For example, the casing 11 can be made of glycol modified polyethylene terephthalate (PETG) copolyester. PETG is generally known for stiffness, high tensile, high compressive and shear strength, and high impact properties. Tensile strength of the casing 11 can range from 15-150 MPa (ISO527), and more particularly 45-60 MPa. The rigidity of the casing 11 prevents compression of the protected medical device and external attachments. For example, because the lip 16 of the casing 11 surrounds the site of the medical device any inward pressure on the casing 11 is transferred outwardly to the surrounding lip 16 leaving the medical device and external attachments undisturbed.

The membrane 14 spanning the hollow interior of the casing 11 can be made of films including polymers such as polyurethane or polyethylene. The membrane 14 also can be made of foams, fibrous products, beads, hydrogels, hydrocolloid dressings, alginates and chitosan. In one embodiment, the membrane 14 is made of perforated plastic film absorbent dressing such as Melolin® (Smith and Nephew Medical Ltd; London, England) or Telfa® (Kendall Ltd; Boston, Mass.), or a vapour permeable film such as Opsite® (Smith and Nephew Medical Ltd; London, England), Tegaderm® (3M Health Care Ltd; St. Paul, Minn.) or Bioclusiveo (Johnson and Johnson Ltd; New Brunswick, N.J.). In one embodiment, the membrane 14 is impervious to all fluids and gases. In another embodiment the membrane 14 can be made of hydrogel dressings such as Intrasite® Gel (Smith and Nephew Medical Ltd; London, England), Granugel (Convatec Ltd; UK), Sterigel (Seton Healthcare Ltd; UK) or Nu-gel® (Johnson and Johnson Medical Ltd; New Brunswick, N.J.). In another embodiment, the membrane 14 is permeable to water vapor and some fluids, but impermeable to microorganisms or particulate, etc. In another embodiment, the membrane 14 includes one or more lower adhesive layers and one or more upper absorbent layers that draw and contact fluid from the patient's tissue through the adhesive layers.

The membrane 14 can be made of an adhesive material or be covered by an adhesive material. The membrane 14 forms a flexible seal and affixes the medical device and connections between the external attachments of the medical device, such as a needle or tubing attached to the needle, preventing their accidental dislodgement or removal. The membrane 14 is at a tension such that it prevents shifting of the applied or inserted medical device and external attachments, but is not so taut that it inwardly compresses the applied or inserted medical device or external attachments, which can cause the patient pain. As a further benefit, the membrane 14 prevents unwanted entry of air into the lines by maintaining connections between parts of the external attachments of the applied or inserted medical device. As described with respect to the casing 11, the membrane 14 can be translucent, semi-transparent or transparent allowing for visual inspection of the affixed devices, external attachments and underlying skin.

The protective dressing 10 can include adhesive seals which help to anchor the protective dressing 10 to a patient's skin. The internal seal 15 communicates with the bottom of the lip 16 of the casing 11 via the outer margin of the membrane 14, the top edge of which is attached to the bottom of the lip 16. The external seal 12 surrounds the outer protuberance of the casing 11. The external seal 12 contacts the lip 16 of the casing 11 on the side of the lip 16 opposite of the internal seal 15 and the membrane 14. The internal seal 15 can be a foam material with adhesive on each side. The internal seal 15 adheres to the patient's skin surrounding the site of the applied or inserted medical device and anchors the protective dressing 10. Further, the internal seal 15 acts to cushion the lip 16 where it contacts the patient's skin for the benefit of comfort to the wearer. The external seal 12 can be a flexible, thin film material such as a polyethylene adhesive film material. For example, latex-free surgical tape, such as Transpore® (3M; St. Paul, Minn.), can be used. The external seal 12 adheres to the patient's skin at the outer perimeter of the applied or inserted medical device site further affixing the protective dressing 10 to the patient's skin.

The membrane 14 adheres to the skin and affixes the applied or inserted medical device and external attachments. The internal seal 15 likewise adheres to the patient's skin and helps to anchor the membrane 14. The external seal 12, with contribution by the internal seal 15 and the membrane 14, collectively adheres the protective dressing 10 to the patient's skin. Each of the membrane 14, internal seal 15 and external seal 12 can be applied, removed and re-applied to the patient's skin without irritation or loss of adhesiveness.

Also shown in FIGS. 3 and 4, each of the casing 11, external seal 12, membrane 14 and internal seal 15 of the protective dressing 10 can have a notch (21, 22, 24 and 25, respectively), which when aligned with one another form a slot 13. The slot 13 can be wide enough to receive devices or external attachments, for example, a tube such as a catheter, and the like. In one embodiment, the slot 13 can have a uniform width allowing devices or external attachments to lie flush with the patient's skin.

Depending on the size of the protective dressing 10 and the size of the device to be protected, the width of the slot 13 can vary. In one embodiment, the width of the slot 13 at the lip 16 of the casing 11 can be at least about 0.005 cm, 0.01 cm, 0.02 cm, 0.03 cm, 0.04 cm, 0.05 cm, 0.1 cm, 0.2 cm, 0.3 cm, 0.4 cm, 0.5 cm, 1 cm, 2 cm, 3 cm, 4 cm or 5 cm.

Depending on the size of the protective dressing 10 and the size of the device to be protected, the length of the slot 13 from the outer edge of the lip 16 of the casing 11 also can vary. In one embodiment, the length of the slot 13 from the outer edge of the lip 16 of the casing 11 can be at least about 0.01 cm, 0.02 cm, 0.03 cm, 0.04 cm or 0.05 cm. In another embodiment, the length of the slot 13 from the outer edge of the lip 16 of the casing 11 can be at least about 0.1 cm, 0.2 cm, 0.3 cm, 0.4 cm, 0.5 cm, 1 cm, 2 cm, 3 cm, 4 cm, 5 cm, 6 cm, 7 cm, 8 cm, 9 cm or 10 cm.

The width of slot 13 can be either uniform or not uniform. For example, the slot 13 can be narrower at the out edge of the lip 16 of the casing 11 than the width of the slot 13 toward the center of the casing 11 (as shown in FIG. 4). This results in the slot 13 having a keyhole shape. The width of the slot 13 at the outer edge of the lip 16 of the casing 11 can be narrow enough to permit a tube T, such as a catheter, to be wedged between the slot in a friction tight manner. Because the width of the slot 13 toward the center of the casing 11 can be a widened terminus, the tube T can rest unrestricted. This allows the applied or inserted medical devices and external attachments, such as a catheter, to be positioned at an angle with respect to a patient's skin. Alternatively, the applied or inserted medical devices and external attachments can lie flush against the skin and not be wedged up at an angle.

The protective dressing 10 can be permeable to both water vapor and oxygen, but impermeable to micro-organisms thereby acting as an effective barrier to external contamination. The casing 11 and membrane 14 can have microscopic pores that allow for the exchange of fluids while restricting movement of larger particles, such as microorganisms or particulate. Further, each of the membrane 14, internal seal 15 and external seal 12 of the protective dressing 10 can be coated or impregnated with an antimicrobial or combination thereof to help reduce the risk of infection at the site of the wound.

To apply the protective dressing 10 to protect and secure a medical device, such as tubing attached to a needle inserted into an implanted port, the backing 17 is removed from the protective dressing 10 exposing the adhesive parts of the protective dressing 10. The adhesive parts of the protective dressing 10 can include the external seal 12, the internal seal 15 and the membrane 14. The lip 16 of the casing 11 is positioned over the site of the medical device, such as an implanted port, such that it surrounds the medical device. The membrane 14 spanning the hollow interior of the casing 11 is placed over the external attachments of the medical device, such as tubing and attached needle, forming an adherent sheath encapsulating the external attachments of the medical device.

The internal seal 15 attached to the lip 16 of the casing 11 is pressed down onto the skin surrounding the site of the medical device and is secured by the adhesive properties or adhesive coating of the internal seal 15. The external attachments of the medical device are now secured and do not move in relation to the patient's skin or to the protective dressing 10. The slot 13 can receive the tubing attached to the needle. The external seal 12 is then pressed down onto the skin. The external seal 12 adheres to the patient's skin at the outer perimeter of the medical device further securing the casing 11 and external attachments of the device in relationship to the patient's skin.

Figure 7:
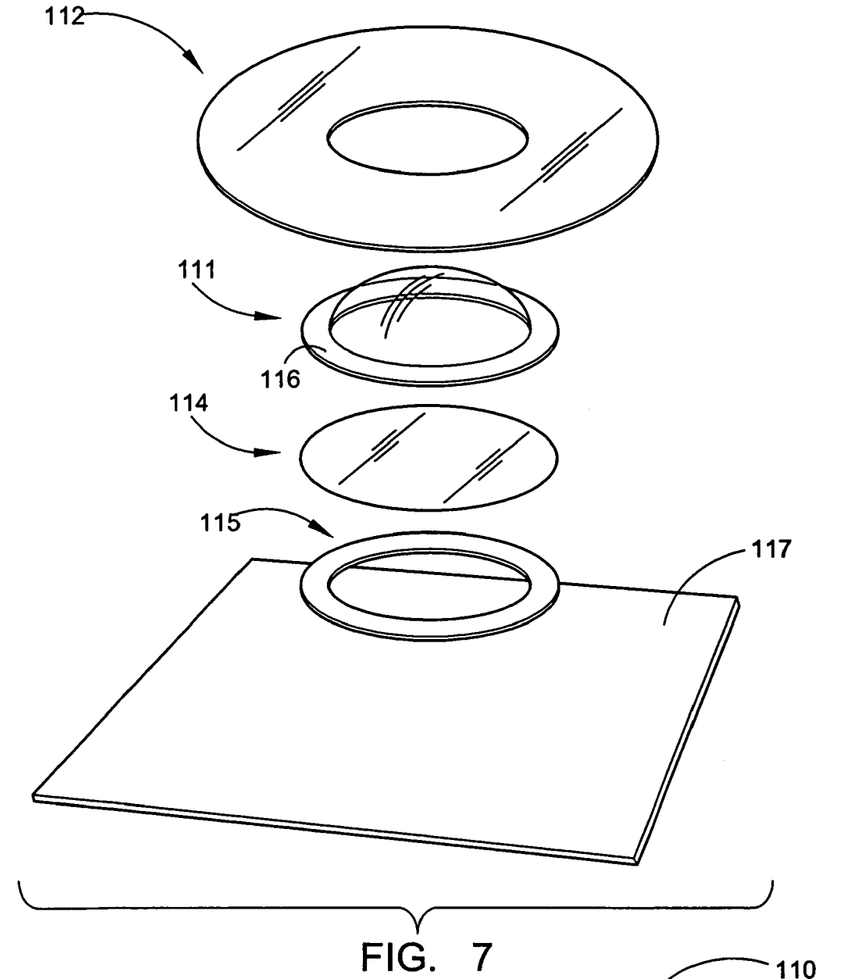
FIG. 7 is an exploded view of another embodiment of a protective dressing.
Figure 8:
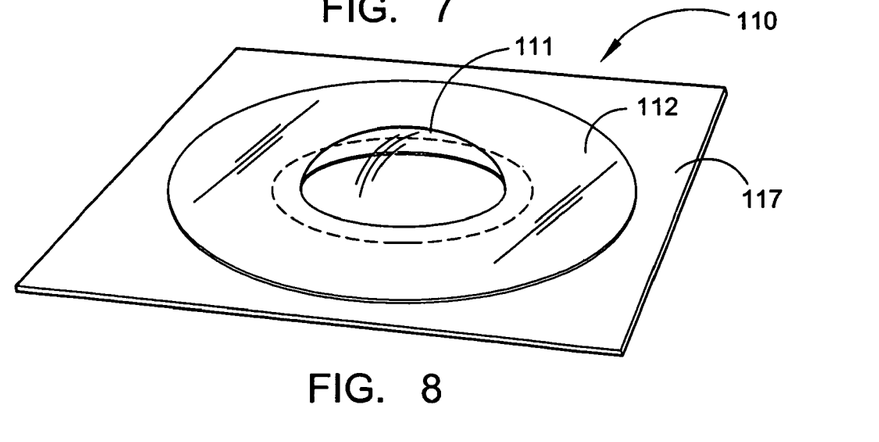
FIG. 8 is a perspective view of the protective dressing of FIG. 7.

FIGS. 7 and 8 show another embodiment of a protective dressing 110 that includes a substantially rigid casing 111, a membrane 114, internal seal 115 and external seal 112. The membrane 114 contacts the patient's skin and the lip 116 of the casing 111 surrounds the wound site. The substantially rigid casing 111 adheres to the patient's skin via the internal seal 115 attached to the lip 116 of the casing and the membrane 114 which spans the hollow interior of the casing 111. The membrane 114 attaches to the casing 111 at the lip 116 by, for example, an adhesive material coating the membrane 114 or due to adhesive properties of the membrane 114 itself.

The internal seal 115 is shaped similarly as the lip 116 of the casing 111 and is attached to the bottom of the lip 116 of the casing 111 via the outer margin of the membrane 114, which is attached to the lip 116. Thus, the internal seal 115 and the lip 116 of the casing 111 sandwich the membrane 114. As described for the membrane 114, the internal seal 115 can be attached to the casing 111 by way of an adhesive material coating the internal seal 115, intrinsic adhesive properties of the internal seal 115 itself or due to an adhesive coating or adhesive properties of the membrane 114. The external seal 112 contacts the top of the lip 116 of the casing 111 (i.e., the side of the lip opposite the internal seal 115 and the membrane 114). The external seal 112 can be attached to the lip 116 due to an adhesive coating on the bottom side of the external seal 112 or other adhesive property of the external seal 112. The external seal 112, internal seal 115 and membrane 114 can be made of adhesive material or coated with an adhesive material. The adhesive parts of the protective dressing 110 can be removeably attached to a backing 117, such as a wax paper backing and the like.

The membrane 114 spanning the hollow interior of the casing 111 can be made of a combination of synthetic and biological materials, such as, dermal replacements made of reconstituted collagen and chondroitin sulfate backed by a polymer layer, or collagen seeded with cells to regenerate the skin. Each of the membrane 114, internal seal 115 and external seal 112 of the protective dressing 110 can be coated or impregnated with an antimicrobial or combination thereof to help reduce the risk of infection at the site of the wound. The membrane 114 also can be made of films including polymers such as polyurethane or polyethylene. The membrane 114 also can be made of foams, fibrous products, beads, hydrogels, hydrocolloid dressings, alginates and chitosan. In one embodiment, the membrane 114 is made of perforated plastic film absorbent dressing such as Meloline® (Smith and Nephew Medical Ltd; London, England) or Telfa® (Kendall Ltd; Boston, Mass.), or a vapour permeable film such as Opsite® (Smith and Nephew Medical Ltd; London, England), Tegaderm® (3M Health Care Ltd; St. Paul, Minn.), or Bioclusive® (Johnson and Johnson Ltd; New Brunswick, N.J.). In one embodiment, the membrane 114 is impervious to all fluids and gases. In another embodiment, the membrane 114 can be made of hydrogel dressings such as Intrasite® Gel (Smith and Nephew Medical Ltd; London, England), Granugel (Convatec Ltd; UK), Sterigel (Seton Healthcare Ltd; UK) or Nu-gel® (Johnson and Johnson Medical Ltd; New Brunswick, N.J.). In another embodiment, the membrane 114 is permeable to water vapor and some fluids, but impermeable to microorganisms or particulate, etc. In another embodiment, the membrane 114 includes one or more lower adhesive layers and one or more upper absorbent layers that draw and contact fluid from the patient's tissue through the adhesive layers.

The protective dressing 110 can be used to prevent irritation and promote wound healing, for example, in the treatment of burns, chronic ulcers and pressure sores, donor sites, post-operative wounds, and a variety of other injuries. In another embodiment, the protective dressing 110 can exclude the membrane 114 such that it covers a wound and comes into contact only with the skin surrounding the wound site, not the wound itself.

The protective dressing 110 can be permeable to both water vapor and oxygen, but impermeable to micro-organisms thereby acting as an effective barrier to external contamination while producing a moist environment at the surface of the wound. The casing 111 and membrane 114 can have microscopic pores that allow for the exchange of fluids while restricting movement of larger particles, such as microorganisms or particulate. In another embodiment, each of the internal 115 and external 112 seals of the protective dressing 110 can form a fluid-tight seal with a patient's skin resulting in the collection of exudate during heavy drainage phases of wound healing. The substantially rigid casing 111 of the protective dressing 110 can be used to cover pressure sores. Pressure sores often occur on the underneath side of immobile or bed-ridden patients. The protective dressing 110 can be worn comfortably by these patients even when covering sores on the underneath side and prevent further compression of pressure ulcers.

Figure 9:
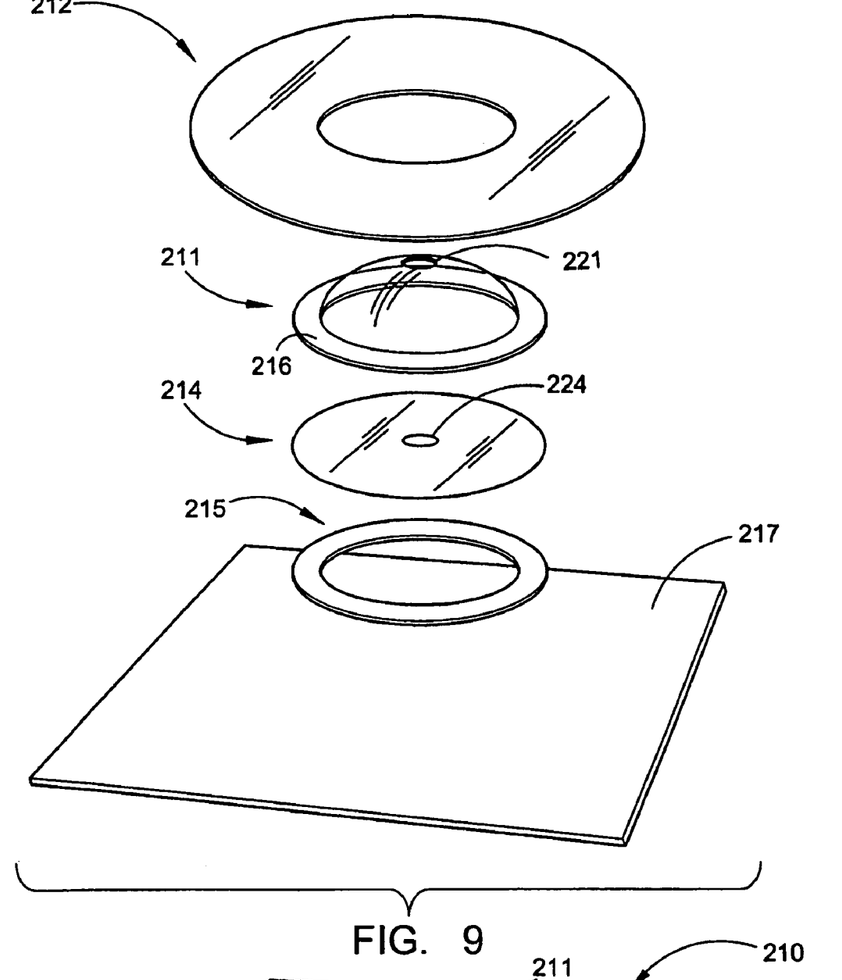
FIG. 9 is an exploded view of another embodiment of a protective dressing.
Figure 10:
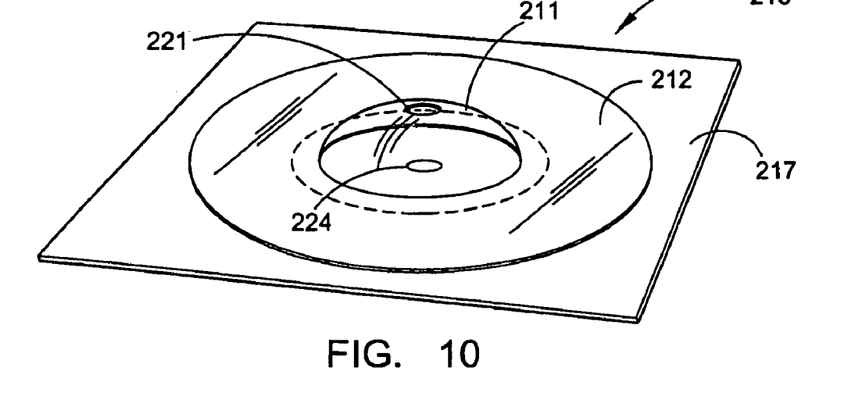
FIG. 10 is a perspective view of the protective dressing of FIG. 9.

In another embodiment (shown in FIGS. 9 and 10), the protective dressing 210 can have perforations that allow for direct access to the protected underlying site. The protective dressing 210 can include a casing 211, external seal 212, membrane 214 and internal seal 215 removeably attached to a backing 217. The casing 211 and/or the membrane 214 can include one or more perforations (221 and 224, respectively) that allow for direct access to the skin and/or medical devices and external attachments. The diameter of perforations 221 and 224 can vary depending, for example, on the size of the protective dressing 210. The diameter of 221 and 224 can vary also depending on the size of the device penetrating the perforation(s). In one embodiment, the diameter of perforations 221 and 224 can be at least about 0.005 cm, 0.01 cm, 0.02 cm, 0.03 cm, 0.04 cm, 0.05 cm, 0.1 cm, 0.2 cm, 0.3 cm, 0.4 cm, 0.5 cm, 1 cm, 2 cm, 3 cm, 4 cm or 5 cm.

Each of the membranes 14, 114 or 214, internal seals 15, 115 or 215 and external seals 12, 112 or 212 can be impregnated or coated with one or more antimicrobials to help reduce the risk of infection at the site of the wound or medical device. Antimicrobials can include: antibiotics (including, but not limited to β-lactams, penicillins, cephalosporins, carbapenems, monobactams, glycopeptides, aminoglycosides, macrolides, tetracyclines, chloramphenicols, clindamycins, vancomycins, streptogramins, oxazolindinones, fluoroquinolones, metronidazoles and sulfonamides), antifungals (including, but not limited to allylamines, non-azole ergosterol biosynthesis inhibitors, antimetabolites, flucytosine, azoles, fluconazole, glucan synthesis inhibitors, caspofungin, polyenes, amphotericin B, and griseofulvin), antiseptic solutions (including, but not limited to benzalkonium chloride, chlorhexidine, hexachlorophine, sulfadiazine, iodine compounds, mercury compounds, alcohol, chloroxylenol, hydrogen peroxide, boric acid and volatile oils such as methyl salicylate) and heavy metals such as silver.

Figure 11:
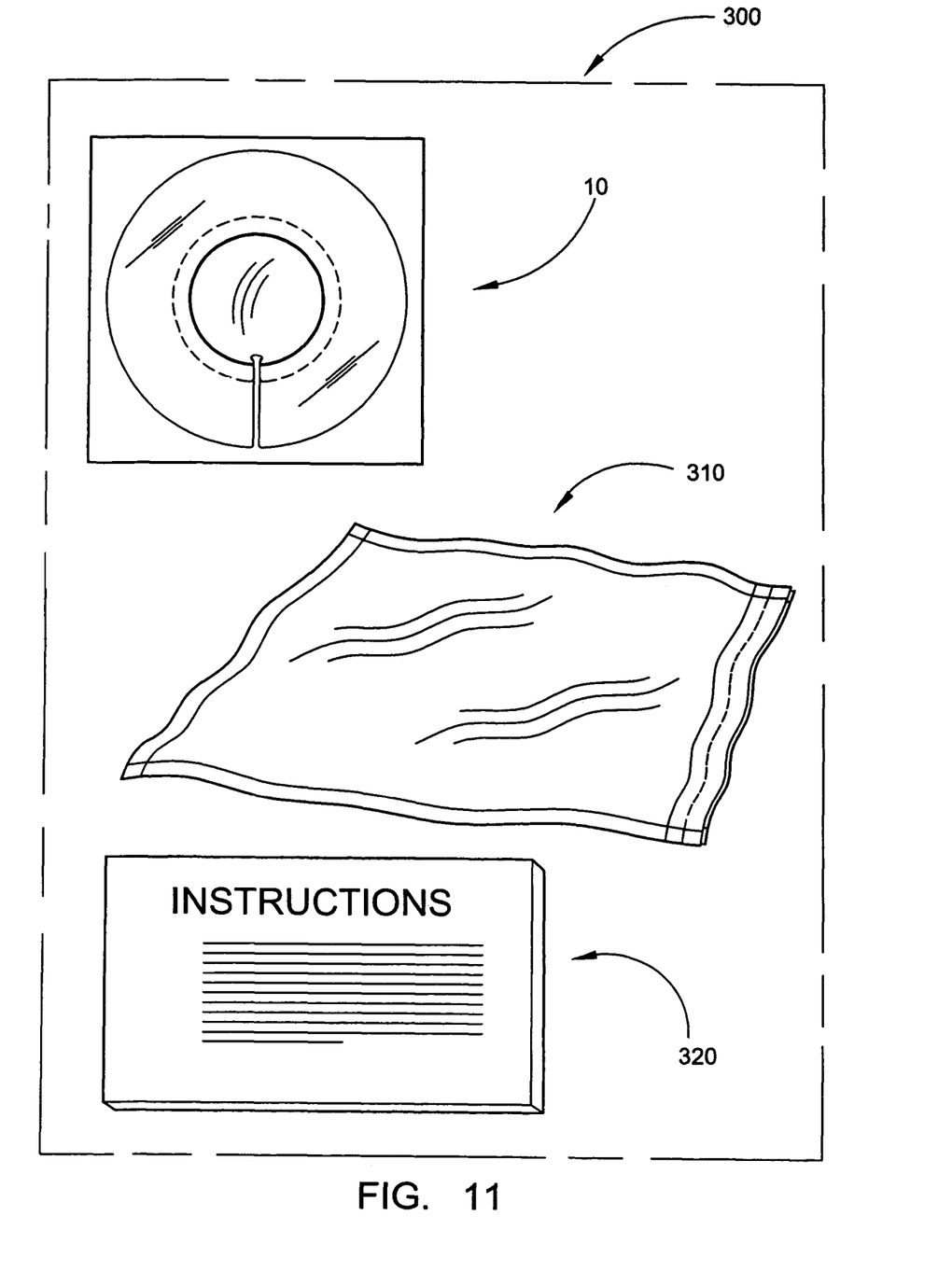
FIG. 11 is an illustration of a protective dressing kit.

As shown in FIG. 11, protective dressings 10, 110 or 210 can be provided as part of a kit 300. The kit 300 generally includes a protective dressing 10, 110 or 210 in a sealed, sterilized packaging container 310 along with a set of instructions 320 describing how to apply the protective dressing 10, 110 or 210 to the patient's skin at a wound site or site of an applied or inserted medical device.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed:

1. A protective device, comprising:
   a substantially rigid casing for placement on a patient's skin so as to prevent compression of a protected medical article, wherein the casing has a hollow interior facing the patient's skin and a lip;
   a membrane spanning the hollow interior of the casing;
   a first adhesive seal attached to a bottom surface of the lip of the casing; and
   a second adhesive seal attached to a top surface of the lip of the casing,
   whereby the membrane is disposed between the casing and the first adhesive seal.
2. The device of claim 1, wherein the casing comprises a transparent, semi-transparent or translucent material.
3. The device of claim 1, wherein the casing comprises a shape selected from the group consisting of spherical, cuboidal, triangular, pyramidal, cylindrical, conical and dome shape.
4. The device of claim 1, wherein the membrane comprises transparent, semi-transparent or translucent material.
5. The device of claim 1, wherein the membrane is impregnated or coated with an antimicrobial agent.
6. The device of claim 5, wherein the antimicrobial agent is selected from the group consisting of β-lactams antibiotics, penicillins, cephalosporins, carbapenems, monobactams, glycopeptides, aminoglycosides, macrolides, tetracyclines, chloramphenicols, clindamycins, vancomycins, streptogramins, oxazolindinones, fluoroquinolones, metronidazoles, sulfonamides, allylamines, non-azole ergosterol biosynthesis inhibitors, antimetabolite antifungals, flucytosine, azole antifungals, fluconazole, glucan synthesis inhibitors, caspofungin, polyene antifungals, amphotericin B, griseofulvin, antiseptic solutions, chloroxylenol, benzalkonium chloride, chlorhexidine, hexachlorophine, sulfadiazine, iodine compounds, mercury compounds, alcohol, hydrogen peroxide, boric acid, volatile oils, methyl salicylate, heavy metals and silver.
7. The device of claim 1, wherein the first adhesive seal is impregnated or coated with an antimicrobial agent.
8. The device of claim 7, wherein the antimicrobial agent is selected from the group consisting of β-lactams antibiotics, penicillins, cephalosporins, carbapenems, monobactams, glycopeptides, aminoglycosides, macrolides, tetracyclines, chloramphenicols, clindamycins, vancomycins, streptogramins, oxazolindinones, fluoroquinolones, metronidazoles, sulfonamides, allylamines, non-azole ergosterol biosynthesis inhibitors, antimetabolite antifungals, flucytosine, azole antifungals, fluconazole, glucan synthesis inhibitors, caspofungin, polyene antifungals, amphotericin B, griseofulvin, antiseptic solutions, chloroxylenol, benzalkonium chloride, chlorhexidine, hexachlorophine, sulfadiazine, iodine compounds, mercury compounds, alcohol, hydrogen peroxide, boric acid, volatile oils, methyl salicylate, heavy metals and silver.
9. The device of claim 1, wherein each of the casing, membrane, first adhesive seal and second adhesive seal comprise a notch.
10. The device of claim 9, wherein the notches are aligned with one another forming a slot.
11. A kit, comprising:
    a protective device comprising:
    a substantially rigid casing for placement on an individual's skin so as to prevent compression of a protected medical article, wherein the casing comprises a hollow interior, a lip, a first adhesive seal attached to a bottom surface of the lip and a membrane disposed between the casing and the first adhesive seal, the membrane spanning the hollow interior;
    a second adhesive seal for attaching the casing to the individual's skin; and
    a backing on which the casing and second adhesive seal are removeably attached; and
    instructions for applying the protective device to the individual's skin.
12. The kit of claim 11, wherein the casing comprises a transparent, semi-transparent or translucent material.
13. The kit of claim 11, wherein the casing comprises a shape selected from the group consisting of spherical, cuboidal, triangular, pyramidal, cylindrical, conical and dome shape.

14. The kit of claim 11, wherein the membrane comprises a transparent, semi-transparent or translucent material.

15. The kit of claim 11, wherein the membrane is impregnated or coated with an antimicrobial agent.

16. The kit of claim 11, wherein each of the casing, membrane, first adhesive seal and second adhesive seal comprise a notch.

17. The kit of claim 16, wherein the notches are aligned with one another forming a slot.

18. A device for protecting a medical article placed on a patient's skin, the device comprising:
 a substantially rigid casing forming a cavity and having a lip, the cavity being sized and shaped to cover a medical article without compressing the medical article against the patient's skin;
 a membrane spaced from the casing and spanning the cavity of the casing;
 a first adhesive seal attached to a bottom surface of the lip of the casing; and
 a second adhesive seal attached to a top surface of the lip of the casing, wherein each of the casing, membrane, first adhesive seal and second adhesive seal comprise a notch, the notches being aligned with one another forming a slot opening into the cavity for receiving a portion of the medical article.

19. The device of claim 18, wherein the slot extends through the lip and towards the cavity, a width of the slot being greater toward the cavity so as to position the portion of the medical article at an angle with respect to the patient's skin.

\* \* \* \* \*